(12) United States Patent
Wandke et al.

(10) Patent No.: US 11,785,700 B2
(45) Date of Patent: Oct. 10, 2023

(54) ELECTRODE ARRANGEMENT FOR FORMING A DIELECTRIC BARRIER PLASMA DISCHARGE

(71) Applicant: CINOGY GMBH, Duderstadt (DE)

(72) Inventors: Dirk Wandke, Heilbad Heiligenstadt (DE); Leonhard Trutwig, Duderstadt (DE); Mirko Hahnl, Berlingerode (DE); Karl-Otto Storck, Duderstadt (DE)

(73) Assignee: CINOGY GMBH, Duderstadt (DE)

( * ) Notice: Subject to any disclaimer, the term of this patent is extended or adjusted under 35 U.S.C. 154(b) by 1040 days.

(21) Appl. No.: 16/329,455

(22) PCT Filed: Jul. 21, 2017

(86) PCT No.: PCT/DE2017/100612
§ 371 (c)(1),
(2) Date: Feb. 28, 2019

(87) PCT Pub. No.: WO2018/059612
PCT Pub. Date: Apr. 5, 2018

(65) Prior Publication Data
US 2019/0223280 A1    Jul. 18, 2019

(30) Foreign Application Priority Data
Sep. 30, 2016   (DE) .................... 10 2016 118 569.8

(51) Int. Cl.
*H05H 1/24*     (2006.01)
*A61N 1/04*     (2006.01)
*A61N 1/44*     (2006.01)

(52) U.S. Cl.
CPC ......... *H05H 1/2406* (2013.01); *A61N 1/0468* (2013.01); *A61N 1/44* (2013.01);
(Continued)

(58) Field of Classification Search
None
See application file for complete search history.

(56) References Cited

U.S. PATENT DOCUMENTS 6,146,599 A  * 11/2000 Ruan .................. B01J 19/088
                                                     422/186.04
6,565,716 B1 *  5/2003 Ruan .................. B01J 19/088
                                                     204/170
(Continued)

FOREIGN PATENT DOCUMENTS

DE   10 2009 047 220 A1   6/2011
DE   10 2009 060 627 A1   6/2011
(Continued)

*Primary Examiner* — Srinivas Sathiraju
(74) *Attorney, Agent, or Firm* — WCF IP

(57) ABSTRACT

The invention relates to an electrode arrangement for forming a dielectric barrier plasma discharge between an electrode (1) supplied with an AC high voltage by a control device (20) and a treatment surface (21) of an electrically conductive body (22), said arrangement functioning as a ground electrode, wherein a dielectric material (8) completely covets the electrode (1) up to the treatment surface (21) and forms a contact side for the surface (21). The electrode arrangement permits effective and homogeneous formation of the plasma (23), in particular for large treatment surfaces (21), because the electrode (1) consists of at least two electrode portions (2, 3) arranged next to one another at the same distance (6) from the contact side and insulated from one another by the dielectric material (8), and because adjacent electrode portions are supplied by the control device with compensating partial AC voltages which are mirror-inverted in terms of the waveform and the voltage level.

7 Claims, 3 Drawing Sheets

(52) U.S. Cl.
CPC ....... *H05H 1/2418* (2021.05); *H05H 2245/34* (2021.05); *H05H 2245/36* (2021.05)

(56) References Cited

U.S. PATENT DOCUMENTS

| | | | | |
|---|---|---|---|---|
| 2010/0320916 | A1* | 12/2010 | Yagi | B01J 19/088 |
| | | | | 315/176 |
| 2011/0298376 | A1* | 12/2011 | Kanegae | H05H 1/4622 |
| | | | | 315/111.51 |
| 2011/0308457 | A1* | 12/2011 | Simor | H05H 1/2439 |
| | | | | 118/723 R |
| 2012/0085900 | A1* | 4/2012 | Verbeck, IV | H01J 49/0027 |
| | | | | 250/288 |
| 2012/0259270 | A1* | 10/2012 | Wandke | A61N 1/40 |
| | | | | 604/23 |
| 2013/0026137 | A1* | 1/2013 | Kindel | H05H 1/2443 |
| | | | | 134/1.1 |
| 2013/0088807 | A1* | 4/2013 | Tojo | H01T 23/00 |
| | | | | 361/231 |
| 2013/0202496 | A1* | 8/2013 | Konesky | H01J 37/244 |
| | | | | 422/186 |
| 2013/0306100 | A1* | 11/2013 | Wandke | H05H 1/2406 |
| | | | | 132/211 |
| 2014/0162338 | A1* | 6/2014 | Schaefer | A61L 2/03 |
| | | | | 315/111.21 |
| 2015/0014183 | A1* | 1/2015 | Akay | B01J 35/002 |
| | | | | 205/462 |
| 2015/0371829 | A1* | 12/2015 | Koyama | H01J 37/32348 |
| | | | | 313/231.31 |
| 2016/0230783 | A1* | 8/2016 | Onishi | F15B 5/006 |
| 2018/0221517 | A1* | 8/2018 | Trutwig | A61B 18/042 |
| 2019/0223280 | A1* | 7/2019 | Wandke | H05H 1/2406 |
| 2020/0029414 | A1* | 1/2020 | Trutwig | A61B 18/042 |
| 2022/0172929 | A1* | 6/2022 | Wandke | H01J 37/32036 |

FOREIGN PATENT DOCUMENTS

| | | |
|---|---|---|
| DE | 10 2011 000 261 A1 | 7/2012 |
| DE | 10 2011 001 416 A1 | 9/2012 |
| DE | 10 2014 013 716 A1 | 3/2016 |
| DE | 20 2007 019 709 U1 | 4/2016 |
| WO | 2009/098662 A1 | 8/2009 |
| WO | 2010/082561 A1 | 7/2010 |
| WO | 2012/163876 A1 | 12/2012 |

\* cited by examiner

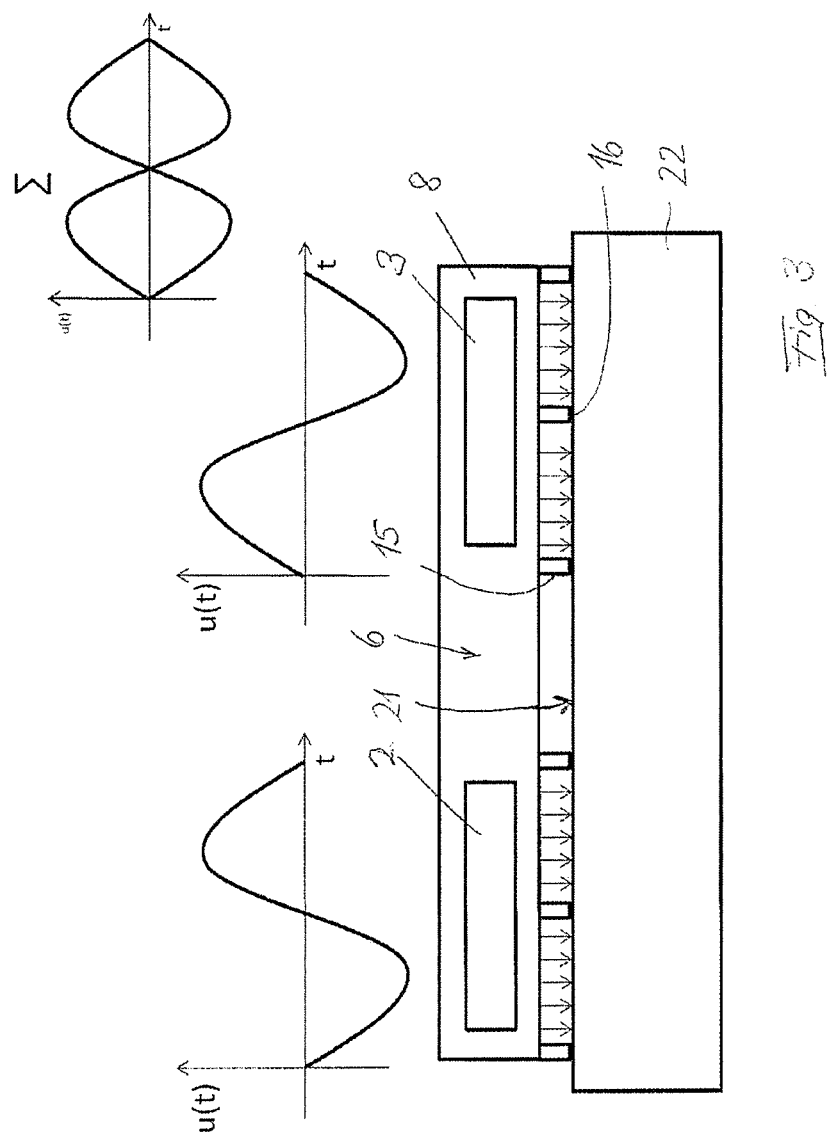

ELECTRODE ARRANGEMENT FOR FORMING A DIELECTRIC BARRIER PLASMA DISCHARGE

The invention relates to an electrode arrangement for forming a dielectric barrier plasma discharge between an electrode fed with a high AC voltage by a control device and a surface to be treated of an electrically conductive body, which serves as a ground electrode, wherein a dielectric completely covers the electrode toward the surface to be treated and forms a bearing side for the surface.

Such a planar electrode arrangement, which may be flexibly formed, is known from DE 10 2009 060 627 B4. The planar electrode is in this case embedded between an underside of the dielectric and an upper side of the dielectric, which respectively extend in surface area beyond the electrode and thus also cover the narrow border of the electrode, so that contact with the electrode carrying the high voltage is ruled out. It is also ruled out that it can come close enough to the electrode for a spark to cross over. Rather, the dielectric prevents a galvanic current flow from the electrode to the surface to be treated, which serves as a ground electrode. The electrode arrangement consequently has no ground electrode of its own. In order to ensure the formation of a plasma in the layer of air between the surface to be treated and the dielectric, in the case of a smooth surface to be treated the underside of the electrode arrangement that is facing the surface to be treated may be formed with protruding nubs, which lie with their upper side on the surface to be treated and have continuous interspaces in which the plasma can form when a high AC voltage is applied to the electrode.

Such an electrode arrangement can be placed onto the surface to be treated, wherein the surface to be treated may in particular be on the skin of a human or animal body. The plasma treatment in this case leads to a disinfection of the skin deep within the pores and improves the absorption capacity of the skin for care products that are applied to the skin to be treated.

It is also known that plasma treatment may be advantageous for healing wounds. According to DE 10 2009 047 220 A1, a pen-like appliance through which a treatment gas flows is used to generate a plasma, which emerges from an end face of the appliance formed in the manner of a nozzle and can be directed onto the skin or wound to be treated.

DE 10 2011 01 416 A1 discloses a planar flexible wound treatment device in which two surface electrodes are formed by interwoven, insulated electrical conductors. The high voltage that is intended to allow a plasma to be created in the air gaps forms between the conductors. This requires that the entire electrode arrangement is gas-permeable.

There are also known electrode arrangements in which a dielectric barrier surface plasma can be produced. WO 2009/098662 A1 describes such an arrangement in which a first planar electrode and a second grid-like electrode are embedded at a distance from one another in the direction of the height of the electrode arrangement in a dielectric, so that an electric field suitable for the formation of a plasma forms on the surface of the dielectric that is near the grid-like electrode. At the grid-like electrode there is a high AC voltage, while the planar electrode located thereunder is at ground potential. Such an arrangement has a high energy requirement and a low efficiency with regard to the formation of the surface plasma.

Advantageous in this respect are electrode arrangements in which the electrode thereof is formed in such a way that a largely homogeneous field pattern is produced between the planar electrode and the surface to be treated as the ground electrode and leads to a defined and ideally uniform plasma.

There is increasingly the need also to treat comparatively large areas by placing on an—in particular flexible—electrode arrangement of the type described. With increasing treatment area, however, it is more difficult to form by the usual technique the field strengths required for the formation of a uniform plasma between the bearing side of the dielectric and the surface to be treated. The invention therefore addresses the problem of forming an electrode arrangement of the type mentioned in such a way that on the one hand a plasma that is as uniform as possible is formed in an efficient way and on the other hand even relatively large areas can be treated with a correspondingly large electrode arrangement with lower expenditure of energy.

To solve this problem, according to the invention an electrode arrangement of the type mentioned at the beginning is characterized in that the electrode consists of at least two partial electrodes which are arranged alongside one another at the same distance from the bearing side and are insulated from one another by the dielectric and in that adjacent partial electrodes are fed by the control device with mutually compensating partial high AC voltages that are inversely equal with respect to the waveform and the voltage magnitude.

The electrode arrangement according to the invention is therefore based on the known principle of using the surface to be treated of the electrically conductive body as a ground electrode, so that in principle only a single electrode is required for the formation of a plasma field and this electrode interacts with the surface to be treated as a ground electrode for the formation of the plasma. This largely produces over the area of the electrode an ideally homogeneous electric field in which the field lines consequently run parallel to one another. As known, it is only at the border of the electrode that curved or oblique field lines may be produced. In the case of the electrode arrangement according to the invention, the partial electrodes are preferably formed (with) and such a surface area that the extent of the electric field (with) and ideally parallel field lines is more than 50%, preferably more than 65% and more preferably more than 80% of the area of the partial electrode. The electrodes according to the invention are of a planar extent and positioned parallel to the bearing side of the dielectric. According to the invention, there are at least two partial electrodes, which are separately supplied with high AC voltages by the control device. The high AC voltages in this case preferably oscillate about the ground potential. Ideally, the high AC voltages could have a sinusoidal characteristic. On account of the capacitances and inductances present in the control device, there may also be oscillating circuit arrangements, with which an excitation pulse respectively triggers a high-frequency oscillation process.

If the partial electrodes arranged alongside one another were activated in phase with one another, ideally a homogeneous plasma would form in the region of the homogeneous field between the partial electrode concerned and the surface to be treated. In the connecting region between the partial electrodes arranged alongside one another, the voltages would however add together and lead to undesired voltage peaks, which would disturb the uniform plasma field. In addition, considerable differences in potential would form within the electrically conducting body on which the surface to be treated is located and these could lead to undesired flows of current within the body. On a living body, this may have unpleasant and possibly dangerous effects.

According to the invention, it is therefore provided that the partial electrodes located alongside one another are activated by inversely equal high AC voltages, so that a substantially field-free separating area is produced in the border regions of the partial electrodes that lie between the adjacent partial electrodes. Since this separating area can be narrow and linear, the disinfecting products formed in the plasma, for example the OH radicals and ozone molecules forming in the air in the plasma, can also be effective in the separating area, since they can, even within their very short lifetime, get into the region of the surfaces in the separating area.

The electrode arrangement according to the invention with its at least two partial electrodes is therefore designed in such a way that ideally the partial electrodes form(s) over their virtually entire area with the surface to be treated a substantially homogeneous field—and with it ideally a uniform plasma—and allow a narrow, in principle field-free, separating area to be produced with respect to the adjacent partial electrode. For two adjacent partial electrodes, therefore, the one partial electrode is activated with a positive half wave of the high AC voltage, while the other partial electrode is activated with a negative half wave, so that in the separating area the two voltages compensate one another. In a preferred embodiment, the respective half waves are identical in size and shape, so that in the separating area there occurs a constant potential which does not change (with the) over the period of the high AC voltage and corresponds to the ground potential of the ground electrode. In practice, the identity of the equal and opposite half waves may only be approximate, so that there is a constant cumulative potential in the separating area even if there is a small fluctuation of the cumulative potential, which is for example less than five percent of the peak voltage. The ideally uniform plasma may in practice be overlaid or disturbed by slight filamentary discharges, even if it is attempted to avoid such filamentary discharges.

The peak voltage of the high AC voltages used expediently lie between ±10 kV and ±100 kV. The alternating frequencies of the high AC voltages expediently lie between a few 100 Hz and approximately 100 MHz.

For adaptation to uneven surfaces, it is expedient if the partial electrodes and the dielectric are flexible. This allows the entire electrode arrangement to follow an irregular surface, so that it can ideally be treated with a uniform plasma field.

In a way known per se, the bearing side of the dielectric that is facing the surface to be treated has a structure, preferably in the form of a grid or nubs, between which the plasma can form when the dielectric lies with the upper side of the nubs or other protruding structures against the surface to be treated.

The electrode arrangement according to the invention can also be formed as a dressing for a wound if the dielectric is formed from a material compatible with a wound, for example suitable silicones, or a layer of a material that is compatible with the wound, for example gauze, is placed on the bearing side of the dielectric.

The electrode arrangement according to the invention is also suitable for draining away fluid from a wound or for feeding in a liquid that heals a wound or promotes the healing of a wound if the dielectric and the partial electrodes have through openings which extend through the electrode arrangement(s) in a height direction and are delimited continuously by the dielectric surrounding the partial electrodes.

The electrode arrangement according to the invention preferably has a high degree of symmetry with respect to the partial electrodes. For this, it is expedient if the partial electrodes have an identical size, so that the area that is effective for the formation of the plasma is distributed uniformly over the number of partial electrodes.

The partial electrodes may consist of a flat metal material which is preferably covered on both sides by a dielectric. However, it is also possible to produce electrodes from a conductive plastic, which can also be connected in a form-fitting manner to the dielectric, which is likewise formed from a plastic, for example silicone. The electrode may for example consist of a silicone with conductive additives, in the form of metal particles, carbon particles or the like.

The invention is to be explained in more detail below on the basis of exemplary embodiments that are represented in the drawings, in which:

FIG. 3 shows a schematic representation of the function of the setting-up principle according to the invention.

Figure 1:
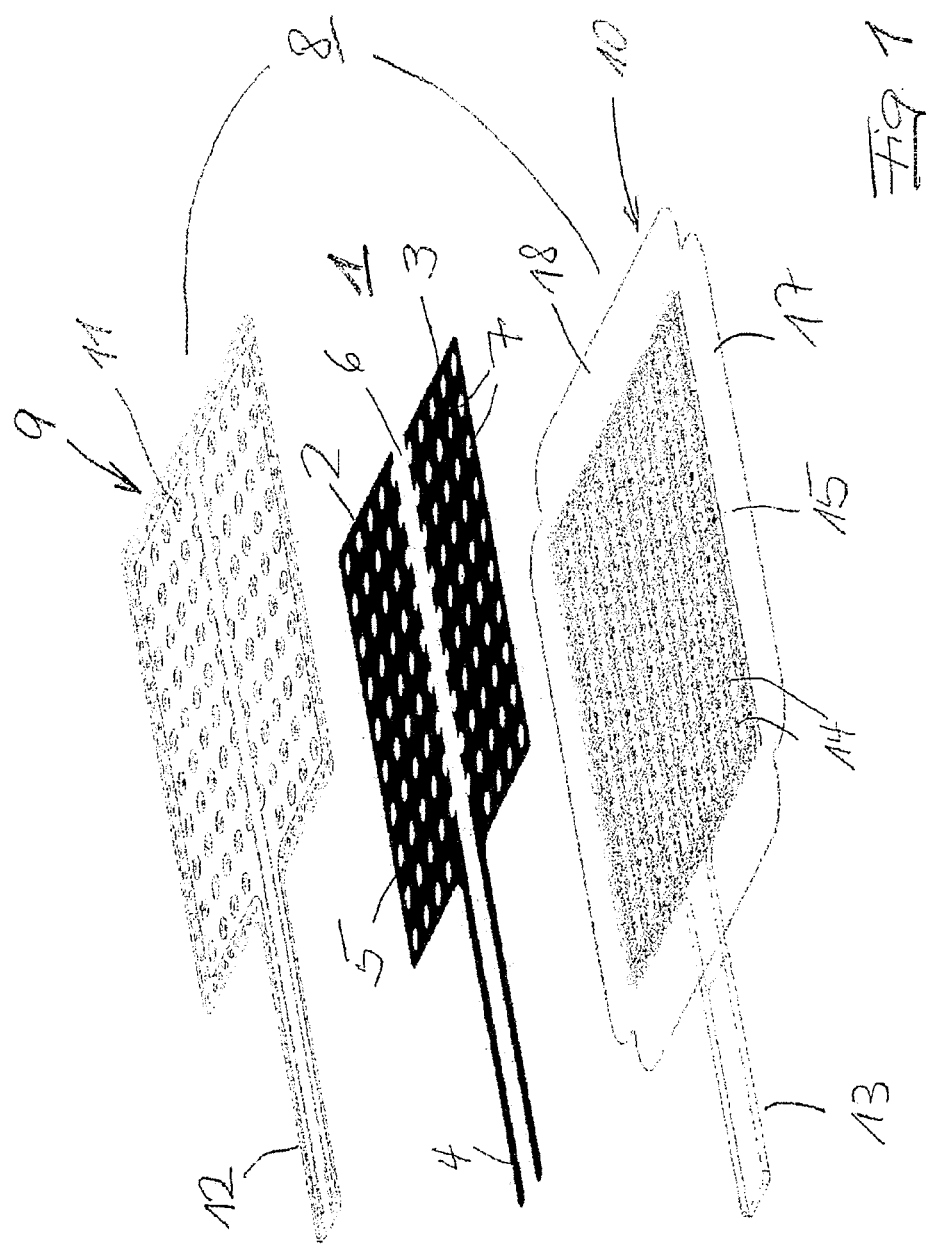
FIG. 1 shows an electrode set-up in an exploded representation.

According to FIG. 1, an electrode 1 is formed by two partial electrodes 2, 3, which are not connected to one another and are at a defined distance from one another. The partial electrodes 2, 3 consist in each case of a narrow flat supply conductor 4, which transforms into a planar formation 5. The planar formations 5 of the two partial electrodes 2, 3 together form an approximately square electrode area, wherein, in the exemplary embodiment represented, there is a distance 6 between the planar formations 5 in the longitudinal direction defined by the supply conductors 4.

The planar formations 5 of the partial electrodes 3 have a number of through openings 7, the function of which is explained in more detail below. As mentioned, the material of the partial electrodes may be a metal foil, a thin metal sheet or a layer of plastic, in particular a layer of silicone, made conductive by the addition of conducting particles.

FIG. 1 reveals that, facing the distance 6, there are in the two planar formations 5 of the partial electrodes 2, 3 approximately semicircular through holes, which bring about a secure interlocking of the partial electrodes with a dielectric filling the distance 6.

The electrode 1 is covered on all sides by a dielectric 8, which in FIG. 1 is shown as consisting of an upper dielectric layer 9 and a lower dielectric layer 10. The upper dielectric layer 5 extends with its area beyond the combined area of the two partial electrodes 2, 3 on all sides and is likewise provided with through openings 11, which are arranged in such a way that they are in line with the through openings 7 of the partial electrodes 2, 3. In the region of the distance 6 between the partial electrodes 2, 3, the upper dielectric layer is solidly formed, in order to bring about a reliable electrical insulation between the partial electrodes 2, 3. Both the upper dielectric layer 9 and the lower dielectric layer 10 have in each case an extension 12, 13, with which the supply conductors 4 are shielded from the surroundings.

The through openings 11 of the upper dielectric layer 9 are formed concentrically with the through openings 7, but have a smaller diameter, so that even in the region of the through openings 7 a layer of the dielectric shields the material of the partial electrodes 2, 3. Therefore, a liquid is also unable to establish a direct electrical connection with the partial electrodes 2, 3.

The lower dielectric layer 10, like the upper dielectric layer 9, forms a continuous cohesive layer. The upper dielectric layer 9 may be interrupted by through openings 14. The through openings 14 are also formed concentrically with the through openings 7 of the partial electrodes and the through openings 11 of the upper dielectric layer. Also in the lower dielectric layer 10, the diameter of the through openings 14 is smaller than the diameter of the through openings 7 of the partial electrodes 2, 3 and the same size as the diameter of the through openings 11 of the upper dielectric layer 9.

On the side facing away from the partial electrodes 2, 3, the lower dielectric layer 10 forms a grid structure 15 with crossing web-like walls, the free edges 16 of which define a bearing side, with which an electrode arrangement can lie on a surface to be treated.

FIG. 1 also reveals that the continuous lower dielectric layer 10 protrudes with lateral strips 17, 18 laterally beyond the contour of the upper dielectric layer 9, and thereby forms extensions with which the electrode arrangement can be secured on the surface to be treated. For this, the lateral strips may be coated with an adhesive agent on their underside or be formed from an adhering material.

Figure 2:
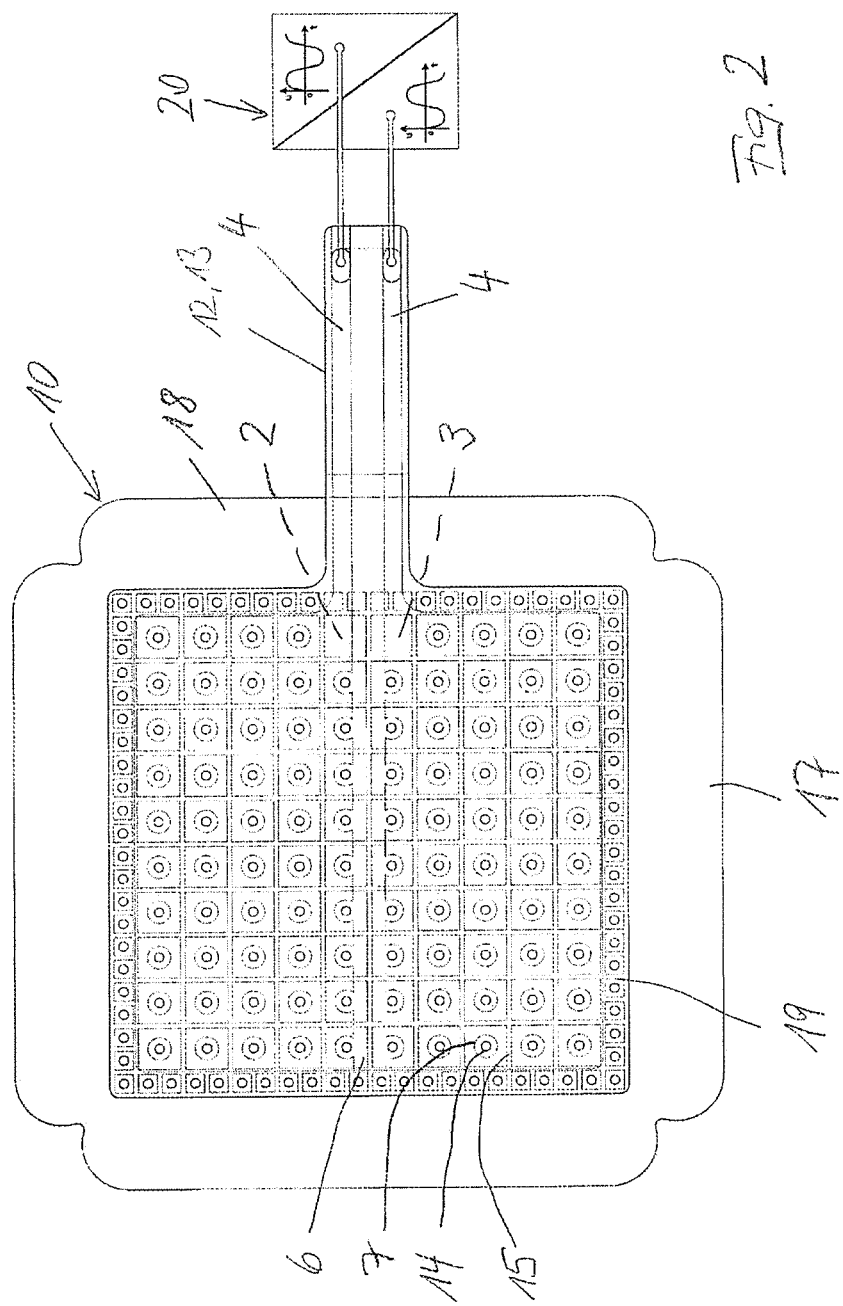
FIG. 2 shows a plan view of a completed electrode arrangement according to FIG. 1

FIG. 2 shows a plan view of the underside, that is to say the bearing side, of the electrode arrangement according to FIG. 1. This representation reveals that the grid structure forms square chambers, in the middle of which are the through openings 14 of the lower dielectric layer, which are arranged concentrically in relation to the (larger) through openings 7 of the partial electrodes 2, 3. In this way, the through openings 7, 14 that are in line with one another form continuous channels, which are delimited on all sides by the material of the dielectric 8 and in particular also shield the material of the partial electrodes 2, 3 in the region of the through openings 7.

FIG. 2 also reveals that the dielectric material is solidly formed in the region of the distance 6 between the partial electrodes 2, 3. Outside the region of the partial electrodes 2, 3, the grid structure 15 is reinforced by a border structure 19 of small chambers arranged in the form of a frame.

In FIG. 2 it is indicated that the supply conductors 4 are contacted by means of a schematically represented contact arrangement in a control device 20. It goes without saying that it must in this case be ensured that there is protection from electric shock with respect to the supply conductors 4 carrying the high voltage. For this, the contacting of the supply conductors 4 may take place for example by insulation cutting contacts, which automatically cut through the material of the dielectric 8 as far as the conducting supply conductors 4 and thereby close an insulating housing. Such insulation cutting contacts are commercially available and need not be explained any more specifically here. However, it is schematically indicated that the supply conductors are supplied with high AC voltages which, when considered over a period, are shifted with respect to one another in such a way that in total they compensate one another, ideally to zero.

The enclosing of the partial electrodes 2, 3 with their supply conductors 4 by the material of the dielectric 8 can be performed in the usual way. In the arrangement according to FIG. 1, the upper dielectric layer 9 and the lower dielectric layer 10 are formed in such a way that they may be welded to one another as thermoplastic material or else just be adhesively bonded to one another. It goes without saying that it is similarly possible to produce the entire dielectric with the inserted partial electrodes 2, 3 in one piece in a molding operation.

FIG. 3 schematically illustrates that the partial electrodes 2, 3 that are embedded in the dielectric 8 and are insulated from one another by way of the distance 6 bring about in the region of the grid structure 15, which acts as a spacer, the formation of a plasma, that as a result is homogeneous, by the electric field triggering the plasma extending homogeneously between the partial electrodes 2, 3 and the surface 21, which is illustrated here by field lines aligned parallel to one another. It is also made clear that no plasma is formed in the region of the distance 6, because this region is virtually field-free. This is attributable to the fact that the two partial electrodes 2, 3 are activated with high AC voltages that are inversely equal with respect to the waveform and magnitude, as is schematically depicted in FIG. 3 above the partial electrodes 2, 3. The likewise depicted cumulative curve E shows that the resultant field in the region of the distance 6 is zero, because the two high AC voltages ideally cancel one another out to zero. This prevents field effects that distort the plasma formation from occurring in the region between the partial electrodes 2, 3. In particular, voltage peaks are avoided.

Formation of the electrode 1 with two partial electrodes 2, 3 is preferred, because it is easiest to accomplish. However, for larger surfaces to be treated it is also conceivable to provide an arrangement with for example four partial electrodes, which for example with four square planar areas 5 form a combined square electrode area. The activation of the partial electrodes would then take place diagonally with the same waveforms and adjacently with equal and opposite waveforms.

It goes without saying that other geometries of the partial electrodes are also conceivable, for example in the form of triangles, rhomboids, hexagons or else circular areas.

The invention claimed is:

1. An electrode arrangement for forming a dielectric barrier plasma discharge between an electrode and a surface to be treated of an electrically conductive body, comprising:
   the electrode;
   a dielectric which completely covers the electrode toward the surface to be treated,
   wherein the dielectric forms a bearing side for contacting the surface to be treated during treatment,
   wherein the electrode comprises at least two partial electrodes which are arranged alongside one another at a same distance from the bearing side of the dielectric,
   wherein the at least two partial electrodes are insulated from one another by the dielectric; and
   a control device connected to the electrode for feeding the at least two partial electrodes with different high AC voltages,
   wherein adjacent partial electrodes of the at least two partial electrodes are fed by the control device with mutually compensating partial high AC voltages that are inversely equal with respect to a waveform and a voltage magnitude,
   wherein the surface to be treated serves as a ground electrode so that a plasma forms between the partial electrodes and the surface to be treated during the treatment,
   wherein the control device comprises a first voltage source which has a pole connected to the first partial electrode for feeding one of the partial high AC voltages,
   wherein the control device comprises a second voltage source which has a pole connected to the second partial electrode for feeding the other of the partial high AC voltages, and
   wherein both partial high AC voltages are mutually compensating with respect to the ground electrode formed by the surface to be treated of the electrically conductive body.

2. The electrode arrangement as claimed in claim 1 wherein the at least two partial electrodes and the dielectric covering the at least two partial electrodes have a planar surface.

3. The electrode arrangement as claimed in claim 1 wherein the at least two partial electrodes and the dielectric covering the at least two partial electrodes are flexible.

4. The electrode arrangement as claimed in claim 1 wherein the bearing side of the dielectric facing the surface to be treated has a structure that forms interspaces when the electrode arrangement bears against the surface to be treated.

5. The electrode arrangement as claimed in claim 1 wherein the at least two partial electrodes and the dielectric covering the at least two partial electrodes each have through openings which extend through the electrode arrangement in a height direction and are delimited continuously by the dielectric covering the at least two partial electrodes.

6. The electrode arrangement as claimed in claim 1 wherein the at least two partial electrodes have an identical size.

7. An electrode arrangement for forming a dielectric barrier plasma discharge between an electrode and a surface to be treated of an electrically conductive body, comprising:
   the electrode;
   a dielectric which completely covers the electrode toward the surface to be treated,
   wherein the dielectric forms a bearing side for contacting the surface to be treated during the treatment,
   wherein the electrode comprises at least two partial electrodes which are arranged alongside one another at a same distance from the bearing side of the dielectric,
   wherein the at least two partial electrodes are insulated from one another by the dielectric; and
   a control device connected to the electrode for feeding the at least two partial electrodes with different high AC voltages,
   wherein adjacent partial electrodes of the at least two partial electrodes are fed by the control device with mutually compensating partial high AC voltages that are inversely equal with respect to a waveform and a voltage magnitude, wherein the surface to be treated serves as a ground electrode so that a plasma forms between the partial electrodes and the surface to be treated during operation,
   wherein the surface to be treated is a skin of human or animal body,
   wherein the control device comprises a first voltage source which has a pole connected to the first partial electrode for feeding one of the partial high AC voltages,
   wherein the control device comprises a second voltage source which has a pole connected to the second partial electrode for feeding the other of the partial high AC voltages, and
   wherein both partial high AC voltages are mutually compensating with respect to the ground electrode formed by the surface to be treated of the electrically conductive body.

* * * * *